US009248035B2

(12) United States Patent
Hoyte et al.

(10) Patent No.: US 9,248,035 B2
(45) Date of Patent: Feb. 2, 2016

(54) FLARED VAGINAL STENT

(71) Applicants: Lennox Hoyte, Tampa, FL (US); Michael J. Casella, Sr., Longwood, FL (US); Karen Bradford, Tampa, FL (US)

(72) Inventors: Lennox Hoyte, Tampa, FL (US); Michael J. Casella, Sr., Longwood, FL (US); Karen Bradford, Tampa, FL (US)

(73) Assignees: UNIVERSITY OF SOUTH FLORIDA, Tampa, FL (US); Casella & Nemcik Enterprises, Inc., Longwood, FL (US); Florida Health Science Center, Inc., Tampa, FL (US)

( * ) Notice: Subject to any disclaimer, the term of this patent is extended or adjusted under 35 U.S.C. 154(b) by 4 days.

(21) Appl. No.: 13/925,297

(22) Filed: Jun. 24, 2013

(65) Prior Publication Data

US 2013/0296643 A1 Nov. 7, 2013

Related U.S. Application Data

(63) Continuation of application No. PCT/US2011/066741, filed on Dec. 22, 2011.

(60) Provisional application No. 61/425,872, filed on Dec. 22, 2010.

(51) Int. Cl.
*A61F 2/82* (2013.01)
*A61F 2/00* (2006.01)

(52) U.S. Cl.
CPC ................ *A61F 2/82* (2013.01); *A61F 2/0045* (2013.01); *A61F 2002/0072* (2013.01)

(58) Field of Classification Search
CPC ............ A61F 2/005; A61F 2/82; A61F 6/08; A61F 6/12; A61F 6/14; A61F 6/142; A61F 6/144; A61F 2/00; A61F 2/0004; A61F 2/0009; A61F 2/0013; A61F 2/0031; A61F 2/0036; A61F 2/004; A61F 2/0045; A61F 2/0063; A61F 2002/0072; A61F 6/00; A61F 6/06; A61M 29/00; A61B 17/42
USPC .......... 600/29, 30, 31, 37; 128/830, 834, 836, 128/837, 838; 606/193
See application file for complete search history.

(56) References Cited

U.S. PATENT DOCUMENTS 2,638,093 A * 5/1953 Kulick ............................ 600/29
4,356,817 A * 11/1982 McKibben et al. ........... 128/838

(Continued)

FOREIGN PATENT DOCUMENTS

WO 2006034719 A1 4/2006
WO WO 2008063085 * 5/2008 ............. A63B 23/20
WO WO 2009078953 * 6/2009 ................ A61F 2/00

OTHER PUBLICATIONS

Christopher D. Adamson, et al., The Vacuum Expandable Condom Mold: A Simple Vaginal Stent for McIndoe-Style Vaginoplast. Ideas and Innovations, Plastic and Reconstructive Surgery, 2004, vol. 113, No. 2, pp. 664-666.

(Continued)

*Primary Examiner* — Charles A Marmor, II
*Assistant Examiner* — Carrie R Dorna
(74) *Attorney, Agent, or Firm* — Smith & Hopen, P.A.; Nilay J. Choksi; Michele L. Lawson

(57) ABSTRACT

A flared vaginal stent having a body portion and an outwardly flared head portion as well as a method of use thereof is presented. The head portion is comprised of an outwardly flared tip, optionally containing a groove to accommodate the cervix, to flatten out the proximal vagina. Anterior surface of the head portion is flat while opposing posterior surface of the head portion is curved. The stent mimics the shape of the human vagina and displays the front and back surfaces of the vagina to facilitate placement and attachment of a graft to the full length of the anterior and posterior walls of the vagina. The flat surface allows suture placement for on the full length of the vagina for attachment of the graft anteriorly. The curved posterior surface highlights the posterior surface of the vagina to aid suture placement on the posterior (underside) of the vagina.

19 Claims, 2 Drawing Sheets

(56) References Cited

U.S. PATENT DOCUMENTS

| | | | | |
|---|---|---|---|---|
| 4,669,478 | A * | 6/1987 | Robertson | 600/300 |
| 6,096,047 | A | 8/2000 | Smit | |
| 6,572,631 | B1 * | 6/2003 | McCartney | 606/167 |
| 2002/0068900 | A1 | 6/2002 | Barnes et al. | |
| 2002/0183711 | A1 | 12/2002 | Moser | |
| 2007/0043388 | A1 | 2/2007 | Greenwood | |
| 2007/0089750 | A1 * | 4/2007 | Astani et al. | 128/830 |
| 2008/0234719 | A1 | 9/2008 | Adams | |
| 2009/0326573 | A1 * | 12/2009 | Miller | 606/193 |
| 2010/0145137 | A1 | 6/2010 | Morgan | |
| 2010/0305394 | A1 * | 12/2010 | Rosenblatt | 600/30 |

OTHER PUBLICATIONS

Ayhan Coskun, et al., The use of a silicone-coated acrylic vaginal stent in McIndoe vaginoplasty and review of the literature concerning silicone-based vaginal stents: a case report. BMC Surgery, 2007, vol. 7, No. 13, pp. 1-4.

International Search Report for International Application No. PCT/US2011/066741, filing date of Dec. 22, 2011, with a mailing date of Aug. 22, 2012.

International Preliminary Report on Patentability for International Application No. PCT/US2011/066741, filed date of Dec. 22, 2011, with a mailing date of Jun. 25, 2013.

* cited by examiner

FLARED VAGINAL STENT

CROSS REFERENCE TO RELATED APPLICATIONS

This application is a continuation of and claims priority to prior filed International Application, Serial Number PCT/US2011/066741 filed Dec. 22, 2011, which is a non-provisional of U.S. Provisional Patent Application 61/425,872, entitled "A Flared Vaginal Stent", filed Dec. 22, 2010, the contents of which are herein incorporated by reference.

FIELD OF INVENTION

This invention relates to medical devices; more specifically, a vaginal stent for use in medical procedures such as the repair of vaginal prolapse.

BACKGROUND OF THE INVENTION

The vagina is a long fibromuscular tube, extending from the perineum, approximately 9-15 centimeters inward and towards the sacrum in the human female. It is attached to the pelvic sidewall on the left and the right, and to the uterosacral ligaments, which pull the apex up towards the sacrum. As the vagina moves inward and to the sacrum, it flares out laterally to maintain attachment to the pelvic sidewall. In women with a uterus, the uterus attaches to the upper middle part of the vagina. The cervix forms the topmost part of the vagina. In cases of vaginal prolapse, the tissues that support the vagina are broken, and the vagina falls outward by telescoping on itself. The definitive way to repair this prolapse, is to push the vagina back in, and hold it in place with a graft, which is attached to the exterior surface of the vagina with sutures. Currently available methods for holding the vagina for suture placement do not duplicate the shape of the vagina appropriately for optimal placement of the attachment sutures and graft.

SUMMARY OF THE INVENTION

The present invention duplicates the shape and length of the vagina so as to present the natural vaginal shape for suture placement and graft attachment. The present invention provides a vaginal stent. The design of the vaginal stent may generally comprise a cylinder with a flared, optionally grooved tip, the flared portion having one partially flat surface and a curved opposite surface. The vaginal stent of the instant invention mimics the internal shape of the vagina and can be modified to accommodate both women having a cervix as well as those without.

Specifically, the vaginal stent includes a body portion and a head portion, each having distal and proximal ends, with the proximal end of the head portion being positioned at the distal end of the body portion. Both portions of the device may be solid and rigid so as to facilitate insertion into the vagina as well as provide a sufficiently hard surface to facilitate placement of the graft on the exterior vagina surface. All surfaces of the graft are preferably smooth.

The head portion of the device has an anterior flat surface and a posterior curved surface with the distal end of the head portion terminating in an outwardly flared tip and head portion tapering inward from distal to proximal end. The outwardly flared tip may be partially curved and have rounded edges. In cross-section, the head portion of the device is substantially hemi-ovoid in shape.

In some embodiments, the outwardly flared tip may contain a groove positioned along the longitudinal axis in the anterior flat surface of the device. This groove is of sufficient size so as to accommodate the cervix of a patient.

The body portion has a straight longitudinal axis and may be of a cylindrical shape or may have anterior and posterior surfaces that correspond to the anterior and posterior surfaces on the head portion, i.e. an anterior flat surface and a posterior curved surface. The proximal end of the body portion of the device may be attached to an elongated handle to facilitate full insertion into the vagina.

A method of facilitating graft placement on an external vaginal wall is also presented. The method comprises providing a vaginal stent having the characteristics described above; inserting the vaginal stent into the vagina of a patient; positioning the vaginal stent within the vagina of the patient so that the anterior flat surface of the head portion of the vaginal stent is positioned adjacent to the anterior internal surface of the vagina and the posterior curved surface of the head portion of the vaginal stent is positioned adjacent to the posterior internal surface of the vagina; making an incision in the abdomen of the patient; pressing the anterior flat surface of the head portion of the vaginal stent against the anterior internal surface of the vagina so as to provide a flat surface on an external surface of the vagina; positioning a graft on the external surface of the vagina on the flat surface created by the vaginal stent; affixing the graft to the external surface of the vagina; removing the vaginal stent from the vagina; and closing the incision in the patient. This method is used for patient not having a cervix.

In women having a cervix, the device with the groove in the flat surface of the head portion described above is used to facilitate graft placement on an external vaginal wall of a patient. In this method, the groove is aligned with the cervix of the patient when positioning the vaginal stent within the vagina of the patient so that the cervix is positioned within the groove.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention provides a vaginal stent. In an embodiment, the design may generally comprise a cylinder with a flared, optionally grooved tip, the flared portion having one partially flat surface and a curved opposite surface. Designed to mimic the shape of the human vagina, the stent is used to display the front and back surfaces of the vagina so as to facilitate placement and attachment of a graft to the full length of the external surface of the anterior and posterior walls of the vagina. The purpose of the flared portion is to flatten out the proximal vagina, in keeping with the natural flared shape of the proximal vagina. The flat surface allows suture placement along the full length of the exterior surface of the vagina for anterior attachment of the graft. The curved posterior surface of the stent highlights the posterior surface of the vagina to aid suture placement on the posterior of the vagina.

Figures 1, 2, 3:
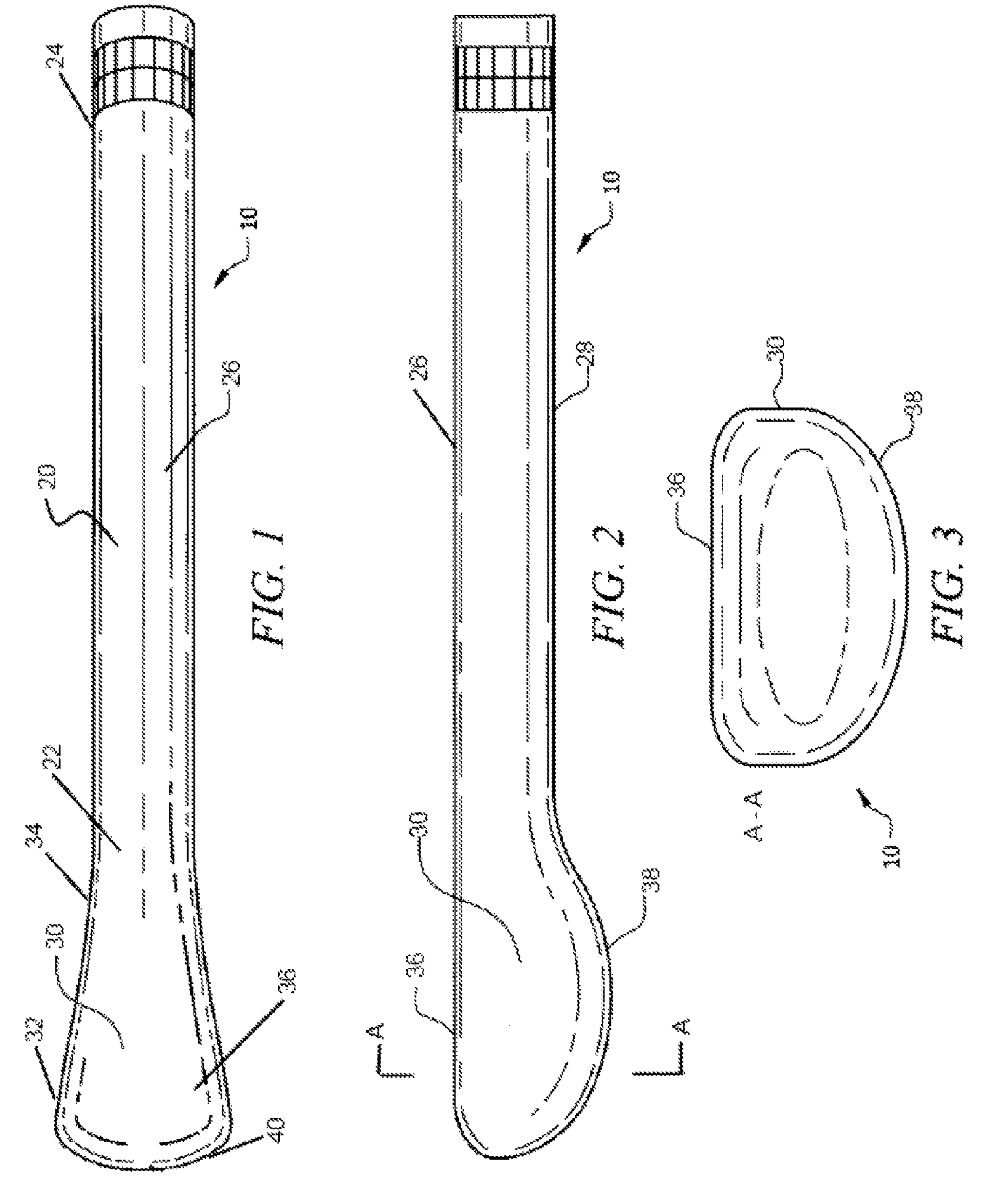
FIG. 1 is a top view of the un-grooved vaginal stent in accordance with an embodiment of the present invention.
FIG. 2 is a side view of the un-grooved vaginal stent in accordance with an embodiment of the present invention.
FIG. 3 is a front view of the un-grooved vaginal stent in accordance with an embodiment of the present invention.

In an embodiment for use in women not having a cervix, vaginal stent 10 is comprised of body portion 20 and head portion 30. As shown in FIGS. 1 and 2, distal end 22 of body portion 20 is congruent with proximal end 34 of head portion 30. Distal end 32 of head portion 30 terminates in outwardly flared tip 40. As shown in FIG. 1, head portion 30 tapers inward from outwardly flared tip 40 at distal end 32 to proximal end 34. Outwardly flared tip 40 may be curved and have rounded edges as illustrated in FIG. 1. Outwardly flared tip 40 is designed to flatten out the proximal vagina, in keeping with the natural flared shape of the proximal vagina Anterior surface 36 of head portion 30 of vaginal stent 10 is flat while posterior surface 38 of head portion 30 of vaginal stent 10 is curved as illustrated in FIG. 2. As illustrated in FIG. 3, a cross-section taken along line A-A reveals that head portion 30 is hemi-ovoid in shape.

Body portion 20 preferably has a straight longitudinal axis with anterior 26 and posterior 28 surfaces. Anterior 26 and posterior 28 surfaces may correspond in shape to anterior 36 and posterior 38 surfaces of head portion 30, i.e. an anterior flat surface and a posterior curved surface. Alternatively, body portion 20 may be cylindrical with curved anterior and posterior surfaces. Proximal end 24 of body portion 20 of the vaginal stent 10 may be attached to an elongated handle to facilitate full insertion into the vagina.

In use in a woman without a cervix, vaginal stent 10 is inserted into the vagina of a patient distally to proximally. The stent 10 positioned within the vagina of the patient so that anterior flat surface 36 of head portion 30 is positioned adjacent to the anterior internal surface of the vagina and posterior curved surface 38 of head portion 30 is positioned adjacent to the posterior internal surface of the vagina. This placement allows the front and back surfaces of the vagina to be displayed so as to facilitate placement and attachment of a graft to the full length of the external (back) surface of the anterior and posterior walls of the vagina. Outwardly flared tip 40 flattens out the proximal vagina, in keeping with the natural flared shape of the proximal vagina. Anterior flat surface 36 of head portion 30 allows suture placement along the full length of the exterior surface of the vagina for anterior attachment of the graft. Posterior curved surface 38 of stent 10 highlights the posterior surface of the vagina to aid in suture placement on the posterior of the vagina.

An incision is then made in the abdomen of the patient. The surgery can be done laparoscopically so as to be less invasive. Stent 10 is then moved to press anterior flat surface 36 of head portion 30 against the anterior internal surface of the vagina. Being that the vagina is elastic, this pressure against the anterior internal surface causes the corresponding external surface to protrude and take on the shape of anterior flat surface 36 of stent 10 thus providing a flat surface on the external vagina onto which a graft may be positioned. The graft is then affixed to the external surface of the vagina. Once the graft is affixed, vaginal stent 10 may be removed from the vagina and the incision in the patient closed.

Figures 4, 5, 6:
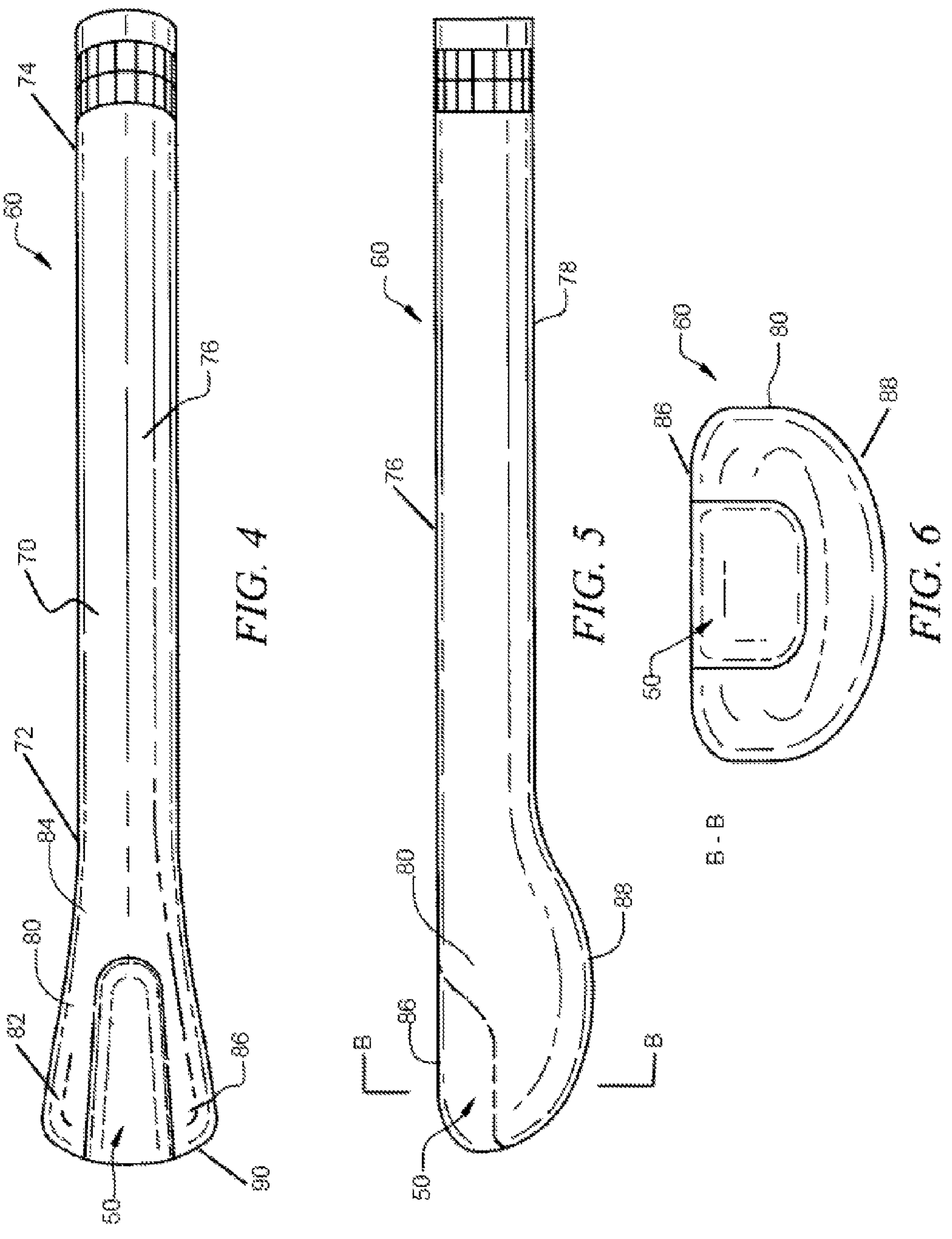
FIG. 4 is a top view of the grooved vaginal stent in accordance with an embodiment of the present invention.
FIG. 5 is a side view of the grooved vaginal stent in accordance with an embodiment of the present invention.
FIG. 6 is a front view of the grooved vaginal stent in accordance with an embodiment of the present invention

In an embodiment for use in women with a cervix, as illustrated in FIGS. 4-6, vaginal stent 60 is comprised of body portion 70 having distal 72 and proximal 74 ends and head portion 80 having distal 82 and proximal 84 ends. As illustrated in FIGS. 4 and 5, and similar to the device used in women without a cervix, distal end 72 of body portion 70 is congruent with proximal end 84 of head portion 80. Distal end 82 of head portion 80 terminates in outwardly flared tip 90. As shown in FIG. 4, head portion 80 tapers inward from outwardly flared tip 90 at distal end 82 to proximal end 84. Outwardly flared tip 90 may be curved and have rounded edges as illustrated in FIG. 4.

Outwardly flared tip 90 may contain groove 50 to accommodate the cervix of a woman. Groove 50 extends longitudinally on anterior surface 86 of head portion 80 from outwardly flared tip 90 in distal end 82 of head portion 80 towards proximal end 84 of head portion 80. Groove 50 is of sufficient depth, width and length so as to accommodate a woman's cervix therein.

Anterior surface 86 of head portion 80 of vaginal stent 60 is flat while posterior surface 88 of head portion 80 of vaginal stent 60 is curved as illustrated in FIG. 5. As illustrated in FIG. 6, a cross-section taken along line B-B reveals that head portion 80 is hemi-ovoid in shape, having a flat anterior surface 86 joined to a curved posterior surface 88. FIG. 3 also illustrates groove 50 positioned substantially centrally on anterior surface 86 of head portion 80.

In use in a woman with a cervix, vaginal stent 60 is inserted into the vagina of a patient distally to proximally. The stent 60 positioned within the vagina of the patient so that anterior flat surface 86 of head portion 80 is positioned adjacent to the anterior internal surface of the vagina and posterior curved surface 88 of head portion 80 is positioned adjacent to the posterior internal surface of the vagina. Groove 50 is aligned with the cervix of the patient so that the cervix is positioned within groove 50. This placement allows the front and back surfaces of the vagina to be displayed so as to facilitate placement and attachment of a graft to the full length of the external surface of the anterior and posterior walls of the vagina. Outwardly flared tip 90 flattens out the proximal vagina, in keeping with the natural flared shape of the proximal vagina. Anterior flat surface 86 of head portion 80 allows suture placement along the full length of the exterior surface of the vagina for anterior attachment of the graft. Posterior curved surface 88 of stent 60 highlights the posterior surface of the vagina to aid in suture placement on the posterior of the vagina.

An incision is then made in the abdomen of the patient. The surgery can be done laparoscopically so as to be less invasive. Anterior flat surface 86 of head portion 80 of stent 60 is pressed against the anterior internal surface of the vagina. Being that the vagina is elastic, this pressure against the anterior internal surface causes the corresponding external surface to protrude and take on the shape of anterior flat surface 86 of stent 60 thus providing a flat surface on the external vagina onto which a graft may be positioned. The graft is then affixed to the external surface of the vagina. Once the graft is affixed, vaginal stent 60 may be removed from the vagina and the incision in the patient closed.

Vaginal stent is shaped to mimic the shape of the interior vagina. Vaginal stent is preferably solid and rigid with all surfaces being smooth so as to provide the necessary firmness needed to form a flat platform for placement of the graft on the exterior vaginal surface as well as to facilitate insertion into the vagina.

The instant invention has several advantages over devices currently used including, but not limited to, having a smooth flat surface for affixing a graft onto the vagina for transabdominal prolapse repair; having an outwardly flared tip which mimics the natural shape of the proximal human vagina; being capable of use in woman with and without a cervix with the optional inclusion of the groove in the distal end of the head portion of the stent; and being capable of presenting the most distal aspects of the posterior vaginal wall for attachment and fixation of the mesh via suturing through the use of the opposing flat and curved surfaces of the stent;

The stent of the present invention duplicates the flared shape of the vagina and presents the anterior and posterior surfaces in such a way to facilitate fixation of a graft to the anterior and posterior surfaces, even in the presence of a cervix, which would otherwise disrupt the vaginal surface and make graft fixation difficult.

It will be seen that the advantages set forth above, and those made apparent from the foregoing description, are efficiently attained, and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. A vaginal stent comprising:
- a solid body portion comprising
  - a distal end and a proximal end; and
  - an anterior surface and a posterior surface;
  - wherein the body portion has a straight longitudinal axis from the distal end to the proximal end;
- a solid head portion comprising
  - a proximal end and a distal end, wherein the proximal end of the head portion is positioned at the distal end of the body portion; and
  - an anterior and a posterior surface, wherein the anterior surface is flat and the posterior surface is curved;
  - wherein the anterior surface of the head portion has an extent that is parallel to a longitudinal extent of the body portion;
  - wherein the anterior surface of the head portion is configured to be pressed along an anterior internal surface of the vagina, such that the anterior flat surface of the head portion presents an outer anterior operational surface of the vagina to which a graft can be positioned;
  - wherein the posterior surface of the head portion is configured to be pressed along a posterior internal surface of the vagina, such that the posterior curved surface of the head portion presents an outer posterior operational surface of the vagina to which a graft can be positioned;
  - wherein the distal end of the head portion terminates in an outwardly flared tip to mimic a natural shape of a human vagina;
  - wherein a distal end of the posterior surface of the head portion curves toward a distal end of the anterior surface of the head portion and terminates in the outwardly flared tip so that the outwardly flared tip is substantially aligned with the flat anterior surface;
  - wherein the head portion tapers inward from distal to proximal end;
- wherein all surfaces of the stent are smooth to facilitate insertion and removal of the vaginal stent into and out of the vagina and to provide a solid surface against which the grafts can be secured.

2. The vaginal stent of claim 1, further comprising:
- a longitudinal groove positioned along the extent of the anterior surface of the distal end of the head portion,
- wherein the groove extends from a distal end of the outwardly flared tip in a proximal direction along the anterior surface of the head portion.

3. The vaginal stent of claim 2, wherein the groove is of sufficient size so as to accommodate a cervix of a patient.

4. The vaginal stent of claim 1, wherein the body portion is substantially hemi-ovoid in shape.

5. The vaginal stent of claim 1, wherein the head portion is substantially hemi-ovoid in cross section.

6. The vaginal stent of claim 1, wherein the outwardly flared tip of the distal end of the head portion is curved.

7. The vaginal stent of claim 6, wherein the outwardly flared tip of the distal end of the head portion contains rounded edges.

8. The vaginal stent of claim 1, wherein the stent is rigid.

9. The vaginal stent of claim 1, wherein the extent of the head portion is co-planar and aligned with the longitudinal extent of the body portion, such that the anterior surface of the head portion is a distal extension of the anterior surface of the body portion.

10. A method of facilitating graft placement on a serosal or peritoneal vaginal wall in a patient via an open or endoscopic trans-peritoneal approach, comprising:
- providing a vaginal stent which mimics the internal shape of a vagina comprising:
  - a solid body portion comprising
    - a distal and a proximal end; and
    - an anterior and a posterior surface;
    - wherein the body portion has a straight longitudinal axis from the distal end to the proximal end;
  - a solid head portion comprising
    - a proximal end and a distal end wherein the proximal end of the head portion is positioned at the distal end of the body portion; and
    - an anterior surface and a posterior surface, wherein the anterior surface is flat and the posterior surface is curved;
    - wherein the anterior surface of the head portion has an extent that is parallel to a longitudinal extent of the body portion;
    - wherein the anterior surface of the head portion is configured to be pressed along an anterior internal surface of the vagina, such that the anterior flat surface of the head portion presents an anterior outer operational peritoneal surface of the vagina to which a first grail can be positioned via the open or endoscopic trans-peritoneal approach;
    - wherein the posterior surface of the head portion is configured to be pressed along a posterior internal surface of the vagina, such that the posterior curved surface of the head portion presents a posterior outer operational peritoneal surface of the vagina to which the graft can be positioned via the open or endoscopic trans-peritoneal approach;
    - wherein the distal end of the head portion terminates in an outwardly flared tip;

wherein a distal end of the posterior surface of the head portion curves toward a distal end of the anterior surface of the head portion and terminates in the outwardly flared tip so that the outwardly flared tip is substantially aligned with the flat anterior surface;

wherein the head portion tapers inward from distal to proximal end;

wherein all surfaces of the stent are smooth to facilitate insertion and removal of the vaginal stent into and out of the vagina;

inserting the vaginal stent into vagina of the patient;

positioning the vaginal stent within the vagina of the patient so that the anterior flat surface of the head portion of the vaginal stent is positioned along an anterior internal surface of the vagina and the posterior curved surface of the head portion of the vaginal stent is positioned along a posterior internal surface of the vagina;

making an abdominal incision in an abdomen of the patient via the open or endoscopic trans-peritoneal approach to surgically enter the abdomen of the patient and access both the anterior outer operational peritoneal vaginal wall and the posterior outer operational peritoneal vaginal wall of the patient;

pressing the anterior flat surface of the head portion of the vaginal stent against an anterior internal surface of the vagina so as to provide a flat, stable surface on the anterior outer operational peritoneal surface of the vagina;

positioning the first graft over the anterior outer operational peritoneal surface of the vagina on the flat, stable surface created by the anterior flat surface of the vaginal stent;

affixing the first graft to the anterior outer operational peritoneal surface of the vagina;

pressing the posterior curved surface of the head portion of the vaginal stent against a posterior internal surface of the vagina so as to provide a stable surface on the posterior outer operational peritoneal surface of the vagina;

positioning the graft over the posterior outer operational peritoneal surface of the vagina on the stable surface created by the posterior curved surface of the vaginal stent;

affixing the graft to the posterior outer operational peritoneal surface of the vagina;

removing the vaginal stent from the vagina; and closing the abdominal incision in the patient.

11. The method of claim 10, wherein the vaginal stent further comprises a longitudinal groove positioned along the extent of the anterior surface of the distal end of the head portion, wherein the groove extends from a distal end of the outwardly flared tip in a proximal direction along the anterior surface of the head portion.

12. The method of claim 11, wherein the groove is of sufficient size so as to accommodate a cervix of the patient.

13. The method of claim 12, further comprising aligning the groove with the cervix of the patient when positioning the vaginal stent within the vagina of the patient wherein the cervix is positioned within the groove.

14. The method of claim 10, wherein the body portion of the vaginal stent is substantially hemi-ovoid in shape.

15. The method of claim 10, wherein the head portion of the vaginal stent is substantially hemi-ovoid in cross section.

16. The method of claim 10, wherein the outwardly flared tip of the distal end of the head portion of the vaginal stent is curved.

17. The vaginal stent of claim 16, wherein the outwardly flared tip of the distal end of the head portion contains rounded edges.

18. The method of claim 10, wherein the vaginal stent is rigid.

19. The method of claim 10, wherein the graft is affixed by sutures.

* * * * *

UNITED STATES PATENT AND TRADEMARK OFFICE

CERTIFICATE OF CORRECTION

PATENT NO. : 9,248,035 B2
APPLICATION NO. : 13/925297
DATED : February 2, 2016
INVENTOR(S) : Lennox Hoyte et al.

It is certified that error appears in the above-identified patent and that said Letters Patent is hereby corrected as shown below:

In the claims,

Column 6, Claim 10, Line 57 should read:

which a first graft can be positioned via the open or

Signed and Sealed this
Twelfth Day of April, 2016

Michelle K. Lee
*Director of the United States Patent and Trademark Office*